(12) United States Patent
Kim et al.

(10) Patent No.: US 11,278,866 B2
(45) Date of Patent: Mar. 22, 2022

(54) SUPER ABSORBENT POLYMER AND ITS PREPARATION METHOD

(71) Applicant: LG Chem, Ltd., Seoul (KR)

(72) Inventors: Su Jin Kim, Daejeon (KR); Dae Woo Nam, Daejeon (KR); Ki Hyun Kim, Daejeon (KR); Joonil Cho, Daejeon (KR)

(73) Assignee: LG Chem, Ltd.

(*) Notice: Subject to any disclaimer, the term of this patent is extended or adjusted under 35 U.S.C. 154(b) by 427 days.

(21) Appl. No.: 16/348,657

(22) PCT Filed: Sep. 4, 2018

(86) PCT No.: PCT/KR2018/010305
§ 371 (c)(1),
(2) Date: May 9, 2019

(87) PCT Pub. No.: WO2019/112150
PCT Pub. Date: Jun. 13, 2019

(65) Prior Publication Data
US 2020/0139344 A1    May 7, 2020

(30) Foreign Application Priority Data

Dec. 8, 2017 (KR) .................. 10-2017-0168684
Sep. 3, 2018 (KR) .................. 10-2018-0104572

(51) Int. Cl.
| | |
|---|---|
| B01J 20/26 | (2006.01) |
| B01J 20/30 | (2006.01) |
| C08F 220/06 | (2006.01) |
| C08J 3/075 | (2006.01) |
| C08J 3/12 | (2006.01) |
| C08J 3/24 | (2006.01) |
| C08L 33/06 | (2006.01) |
| C08K 3/30 | (2006.01) |

(52) U.S. Cl.
CPC ......... B01J 20/261 (2013.01); B01J 20/3021 (2013.01); B01J 20/3085 (2013.01); C08F 220/06 (2013.01); C08J 3/075 (2013.01); C08J 3/12 (2013.01); C08J 3/245 (2013.01); C08L 33/068 (2013.01); B01J 2220/68 (2013.01); C08K 2003/3081 (2013.01)

(58) Field of Classification Search
CPC ...... B01J 20/26; B01J 20/261; B01J 20/3021; B01J 20/3085; B01J 2220/68; C08F 220/06; C08F 3/075; C08F 3/12; C08F 3/245; C08L 33/068; C08K 2003/3081
USPC ....................................................... 502/402
See application file for complete search history.

(56) References Cited

U.S. PATENT DOCUMENTS

| | | |
|---|---|---|
| 4,351,922 A | 9/1982 | Yoshida et al. |
| 4,883,478 A | 11/1989 | Lerailler et al. |
| 5,624,967 A | 4/1997 | Hitomi et al. |
| 7,179,862 B2 | 2/2007 | Mertens et al. |
| 7,285,599 B2 | 10/2007 | Mertens et al. |
| 2009/0157027 A1 | 6/2009 | Kamphus et al. |
| 2009/0182294 A1 | 7/2009 | Ikeuchi et al. |
| 2009/0208748 A1 | 8/2009 | Torii et al. |
| 2011/0095227 A1 | 4/2011 | Herth et al. |
| 2012/0309619 A1 | 12/2012 | Kwon et al. |
| 2013/0172180 A1 | 7/2013 | Naumann et al. |
| 2014/0193641 A1 | 7/2014 | Torii et al. |
| 2016/0220981 A1 | 8/2016 | Yim et al. |
| 2017/0073478 A1 | 3/2017 | Joo et al. |
| 2018/0105655 A1 | 4/2018 | Matsubara et al. |
| 2018/0244868 A1 | 8/2018 | Lee et al. |
| 2018/0257059 A1 | 9/2018 | Heo et al. |

FOREIGN PATENT DOCUMENTS

| | | |
|---|---|---|
| CN | 103619919 A | 3/2014 |
| EP | 0686650 A1 | 12/1995 |
| EP | 3269757 A1 | 1/2018 |
| JP | 2005021704 A | 1/2005 |
| JP | 2010502415 A | 1/2010 |
| JP | 2011511653 A | 4/2011 |
| JP | 2012001735 A | 1/2012 |
| JP | 2017185485 A | 10/2017 |
| JP | 6340348 B2 | 6/2018 |
| KR | 20020064953 A | 8/2002 |
| KR | 20110092236 A | 8/2011 |
| KR | 20140107491 A | 9/2014 |
| KR | 20150033629 A | 4/2015 |
| KR | 101564526 B1 | 10/2015 |
| KR | 20160016714 A | 2/2016 |
| KR | 20160115561 A | 10/2016 |
| KR | 20170052901 A | 5/2017 |
| KR | 20170057705 A | 5/2017 |

(Continued)

OTHER PUBLICATIONS

G. Odian: "Principles of Polymerization", A Wiley-Interscience Publication, year 1981, p. 203.

(Continued)

*Primary Examiner* — Edward M Johnson
(74) *Attorney, Agent, or Firm* — Lerner, David, Littenberg, Krumholz & Mentlik, LLP

(57) ABSTRACT

The present disclosure relates to a super absorbent polymer exhibiting improved rewetting property and excellent absorption property, and a preparation method of the same. This preparation method of a super absorbent polymer includes the steps of: preparing a base resin in which an acrylic acid-based monomer having at least partially neutralized acidic groups and an internal cross-linking agent are cross-linked and polymerized; and heating the base resin in the presence of a surface cross-linking agent to carry out surface modification, wherein the internal cross-linking agent includes a poly(meth)acrylate of polyols-based first internal cross-linking agent and a polyglycidyl ether of polyols-based second internal cross-linking agent in a specific weight ratio.

4 Claims, No Drawings

(56) References Cited

FOREIGN PATENT DOCUMENTS

| KR | 20170106111 A | 9/2017 |
| KR | 20170125388 A | 11/2017 |
| WO | 87003208 A1 | 6/1987 |
| WO | 0145758 A1 | 6/2001 |
| WO | 2016143736 A1 | 9/2016 |

OTHER PUBLICATIONS

International Search Report for Application No. PCT/KR2018/010305 dated Jan. 9, 2019.
R. Schwalm: "UV Coatings: Basics, Recent Developments and New Application (Elsevier 2007)", Elsevier Science (Dec. 21, 2006), p. 115.
Buchholz et al., "Modern Superabsorbent Polymer Technology", Wiley-VCH, 1998, pp. 1-46.
Third Party Observation for Application No. PCT/KR2018/010305 dated Mar. 4, 2020, 6 pages.
Extended European Search Report including Written Opinion for Application No. EP18857399.2 dated Dec. 11, 2019.

SUPER ABSORBENT POLYMER AND ITS PREPARATION METHOD

CROSS-REFERENCE TO RELATED APPLICATIONS

The present application is a national phase entry under 35 U.S.C. § 371 of International Application No. PCT/KR2018/010305, filed on Sep. 4, 2018, which claims priority from Korean Patent Applications No. 10-2017-0168684 filed on Dec. 8, 2017 and No. 10-2018-0104572 filed on Sep. 3, 2018 the disclosures of which are incorporated herein by reference in their entirety.

TECHNICAL FIELD

The present disclosure relates to a super absorbent polymer exhibiting improved rewetting property and excellent absorption property, and a preparation method of the same.

BACKGROUND

A super absorbent polymer (SAP) is a type of synthetic polymeric material capable of absorbing 500 to 1000 times its own weight of moisture. Various manufacturers have denominated it with different names, such as SAM (Super Absorbency Material), AGM (Absorbent Gel Material), and the like. Such super absorbent polymers started to be practically applied in sanitary products, and they are now being widely used not only for hygiene products such as disposable diapers for children, etc., but also for water retaining soil products for gardening, water stop materials for the civil engineering and construction, sheets for raising seedling, fresh-keeping agents for food distribution fields, materials for poultices, or the like.

In most cases, the super absorbent polymer is widely used in the field of hygiene products such as diapers and sanitary napkins, and, for this purpose, it is necessary to exhibit a high absorption capacity for moisture and the like. In addition, it is necessary that the absorbed moisture should not leak out even under external pressure. Further, it needs to show excellent permeability by maintaining its shape even in an expanded (swelled) state after absorbing water.

However, it has been known that it is difficult to improve both the water retention capacity (CRC) indicating basic absorption capacity and water retention ability of the super absorbent polymer, and the absorption ability under pressure (AUP) indicating the characteristic of holding the absorbed moisture even under external pressure together. This is because, when the overall cross-link density of the super absorbent polymer is controlled to be low, the CRC may relatively increase, but the AUP may decrease because the cross-linked structure becomes loose and the gel strength is reduced. On the other hand, when the cross-linking density is controlled to be high for improving the AUP, the basic CRC may decrease because moisture is hardly absorbed through the dense cross-linked structure.

However, recently, hygiene products such as diapers and sanitary napkins have become thinner, and higher absorption performance has been required for the super absorbent polymer. Among these, it becomes important tasks to improve both the water retention capacity and the absorption ability under pressure, which are opposite physical properties, and to improve liquid permeability.

In addition, the hygiene products such as diapers and sanitary napkins may be subjected to pressure by the weight of a user. In particular, when the super absorbent polymer applied to hygiene products such as diapers and sanitary napkins absorbs liquid and a pressure due to the weight of the user is applied to the absorbent polymer, a rewetting phenomenon and a urine leakage phenomenon in which some liquid absorbed in the super absorbent polymer is re-exuded may occur.

Accordingly, various attempts have been made to reduce such rewetting phenomenon. However, a concrete method to effectively inhibit the rewetting phenomenon has not yet been proposed.

Technical Problem

Accordingly, the present disclosure provides a super absorbent polymer exhibiting improved rewetting property while having excellent basic absorption properties such as water retention capacity and absorption ability under pressure, and a preparation method of the same.

Technical Solution

The present disclosure provides a preparation method of a super absorbent polymer, including the steps of:
  preparing a base resin in which an acrylic acid-based monomer having at least partially neutralized acidic groups and an internal cross-linking agent are cross-linked and polymerized; and
  heating the base resin in the presence of a surface cross-linking agent and a polyvalent metal salt to carry out surface modification,
  wherein the internal cross-linking agent includes a poly(meth)acrylate of polyols-based first internal cross-linking agent and a polyglycidyl ether of polyols-based second internal cross-linking agent in a weight ratio of 1:20 to 1:300.

The present disclosure also provides a super absorbent polymer, including:
  a base resin including a cross-linked polymer obtained by cross-linking an acrylic acid-based monomer having at least partially neutralized acidic groups by a medium of an internal cross-linking agent;
  a surface cross-linked layer formed on a particle surface of the base resin, wherein the cross-linked polymer is additionally cross-linked by a medium of a surface cross-linking agent; and
  a polyvalent metal salt formed on the surface cross-linked layer,
  wherein the internal cross-linking agent comprises a poly(meth)acrylate of polyols-based first internal cross-linking agent and a polyglycidyl ether of polyols-based second internal cross-linking agent in a weight ratio of 1:20 to 1:300.

Advantageous Effects

According to the present disclosure, a super absorbent polymer exhibiting excellent absorption properties and suppressing a rewetting phenomenon and a urine leakage phenomenon can be provided.

DETAILED DESCRIPTION OF THE EMBODIMENTS

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

Hereinafter, the preparation method of the super absorbent polymer and the super absorbent polymer prepared by the same according to the embodiments of the present disclosure will be described in more detail.

The present disclosure provides a preparation method of a super absorbent polymer, including the steps of:

preparing a base resin in which an acrylic acid-based monomer having at least partially neutralized acidic groups and an internal cross-linking agent are cross-linked and polymerized; and heating the base resin in the presence of a surface cross-linking agent and a polyvalent metal salt to carry out surface modification, wherein the internal cross-linking agent includes a poly(meth)acrylate of polyols-based first internal cross-linking agent and a polyglycidyl ether of polyols-based second internal cross-linking agent in a weight ratio of 1:20 to 1:300.

In the following specification, the term "base resin" or "base resin powder" means a polymer in the form of particles or powders obtained by polymerizing a water-soluble ethylene-based unsaturated monomer, typically an acrylic acid-based monomer of acrylic acid and/or its salt, followed by drying, pulverizing and classifying. It refers to a polymer in a state in which the surface modification or surface cross-linking step described below is not performed.

The hydrogel polymer obtained by the polymerization reaction of the acrylic acid-based monomer is subjected to drying, pulverizing, classifying, surface cross-linking and the like, and is marketed as a powdery super absorbent polymer product.

In recent years, not only absorption properties such as absorption capacity and liquid permeability but also how dryness of the surface can be maintained in a situation where diapers are actually used is an important measure for evaluating diaper characteristics.

As a result of continuous experiments conducted by the inventors of the present invention, it has been found that the super absorbent polymer obtained by the preparation method according to one embodiment of the present disclosure is superior in absorption properties such as water retention ability, absorption capacity under pressure and liquid permeability and kept dry even after being swollen with salt water, and it is possible to effectively prevent a rewetting phenomenon and a urine leakage phenomenon in which some urine absorbed in the super absorbent polymer is re-exuded. And the invention was completed. This is because the internal cross-linking structure of the base resin and the super absorbent polymer including the same can be optimized by using the internal cross-linking agent with a specific combination and composition, and further, the cross-linking structure and gel strength of the surface cross-linked layer are optimized by using the polyvalent metal salt in the surface cross-linking to make the super absorbent polymer retain moisture once absorbed, despite the external pressure and the like.

In the preparation method of a super absorbent polymer according to one embodiment of the present disclosure, a monomer composition, which is a raw material of the super absorbent polymer, including an acrylic acid-based monomer having at least partially neutralized acidic groups, the first and second internal cross-linking agents and a polymerization initiator, is first polymerized to obtain a hydrogel polymer, and then dried, pulverized and classified to prepare a base resin.

This will be described in more detail below.

The monomer composition which is a raw material of the super absorbent polymer includes an acrylic acid-based monomer having at least partially neutralized acidic groups and a polymerization initiator.

The acrylic acid-based monomer is a compound represented by the following Chemical Formula 1:

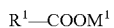  [Chemical Formula 1]

in Chemical Formula 1, $R^1$ is a C2 to C5 alkyl group having an unsaturated bond, and $M^1$ is a hydrogen atom, a monovalent or divalent metal, an ammonium group, or an organic amine salt.

Preferably, the acrylic acid-based monomer includes at least one selected from the group consisting of acrylic acid, methacrylic acid, and a monovalent metal salt, a divalent metal salt, an ammonium salt, and an organic amine salt thereof.

Herein, the acrylic acid-based monomers may be those having acidic groups which are at least partially neutralized. Preferably, the monomers may be those partially neutralized with an alkali substance such as sodium hydroxide, potassium hydroxide, ammonium hydroxide, or the like. In this regard, a degree of neutralization of the acrylic acid-based monomer may be 40 to 95 mol %, 40 to 80 mol %, or 45 to 75 mol %. The degree of neutralization may vary depending on the final physical properties. An excessively high degree of neutralization causes the neutralized monomers to be precipitated, and thus polymerization may not readily occur, whereas an excessively low degree of neutralization not only deteriorates the absorbency of the polymer, but also endows the polymer with hard-to-handle properties, such as those of an elastic rubber.

The concentration of the acrylic acid-based monomer may be 20 to 60 wt %, preferably 40 to 50 wt % based on the monomer composition including the raw material of the super absorbent polymer and a solvent, and properly controlled in consideration of polymerization time and reaction conditions. However, when the concentration of the monomer is excessively low, the yield of the super absorbent polymer may become low and economical efficiency may be reduced. On the contrary, when the concentration of the monomer is excessively high, there is a process problem that part of the monomers is precipitated, or pulverization efficiency is lowered upon pulverization of the polymerized hydrogel polymer, and the physical properties of the super absorbent polymer may be deteriorated.

In the preparation method of a super absorbent polymer of one embodiment, a polymerization initiator that has been generally used for preparing a super absorbent polymer can be applied without particular limitations.

Specifically, the polymerization initiator may be an initiator for thermal polymerization or an initiator for photo-polymerization by UV radiation according to the polymerization method. However, even when the photopolymerization method is applied thereto, a certain amount heat is generated by UV radiation and the like, and some heat occurs as the polymerization reaction, an exothermal reaction, progresses. Therefore, the composition may additionally include the thermal polymerization initiator.

Here, any compound which can form a radical by light such as UV rays may be used as the photopolymerization initiator without limitation.

For example, the photopolymerization initiator may be one or more compounds selected from the group consisting of benzoin ether, dialkyl acetophenone, hydroxyl alkylketone, phenyl glyoxylate, benzyl dimethyl ketal, acyl phosphine, and α-aminoketone. Further, as the specific example of acyl phosphine, commercial Lucirin TPO, namely, 2,4,6-trimethyl-benzoyl-trimethyl phosphine oxide, may be used. More various photopolymerization initiators are well disclosed in "UV Coatings: Basics, Recent Developments and New Application (Elsevier, 2007)" written by Reinhold Schwalm, p 115, and the present invention is not limited thereto.

The concentration of the photopolymerization initiator in the monomer composition may be about 0.01 to about 1.0 wt %. When the concentration of the photopolymerization initiator is excessively low, the polymerization rate becomes slow, and when the concentration of the photopolymerization initiator is excessively high, the molecular weight of the super absorbent polymer becomes low and the properties may be uneven.

Furthermore, as the thermal polymerization initiator, one or more initiators selected from the group consisting of a persulfate-based initiator, an azo-based initiator, hydrogen peroxide, and ascorbic acid may be used. Specifically, sodium persulfate ($Na_2S_2O_8$), potassium persulfate ($K_2S_2O_8$), ammonium persulfate (($NH_4)_2S_2O_8$), and the like may be used as examples of the persulfate-based initiators; and 2,2-azobis-(2-amidinopropane)dihydrochloride, 2,2-azobis-(N,N-dimethylene)isobutyramidinedihydrochloride, 2-(carbamoylazo)isobutylonitril, 2,2-azobis-[2-(2-imidazolin-2-yl)propane]dihydrochloride, 4,4-azobis-(4-cyanovaleric acid), and the like may be used as examples of azo-based initiators. More various thermal polymerization initiators are well disclosed in "Principle of Polymerization (Wiley, 1981)" written by Odian, p 203, and the present invention is not limited thereto.

According to one embodiment of the present disclosure, the monomer composition includes an internal cross-linking agent as a raw material of the super absorbent polymer. This internal cross-linking agent is for cross-linking the interior of the polymerized polymer of the acrylic acid-based monomer, that is, a base resin, and is distinguished from a surface cross-linking agent for cross-linking the surface of the polymer.

In the embodiment of the present disclosure, a poly(meth)acrylate of polyols-based first internal cross-linking agent and a polyglycidyl ether of polyols-based second internal cross-linking agent are used in combination in a weight ratio of 1:20 to 1:300, 1:20 to 1:250, 1:22 to 1:245, or 1:25 to 1:240. Thus, the rewetting property can be further improved while maintaining excellent basic absorbency of the super absorbent polymer prepared by the above-mentioned method, for example, the water retention capacity and the absorption ability under pressure, and the absorption rate. When the weight ratio of the first and second internal cross-linking agents is out of the range, the basic absorbency may be deteriorated or the rewetting property may not be improved.

As the first internal cross-linking agent, a poly(meth)acrylate of polyols-based compound, for example, a poly(meth)acrylate of polyols-based compound having 2 to 10 carbon atoms can be used. For example, at least one selected from the group consisting of trimethylolpropane tri(meth)acrylate, ethylene glycol di(meth)acrylate, polyethylene glycol di(meth)acrylate, propylene glycol di(meth)acrylate, polypropylene glycol di(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate and pentaerythritol tetraacrylate can be used.

As the second internal cross-linking agent, a polyglycidyl ether of polyols-based compound having a polyfunctional epoxy group, for example, a polyglycidyl ether of polyols-based compound having 2 to 10 carbon atoms can be used. For example, at least one selected from the group consisting of ethyleneglycol diglycidyl ether, polyethylene glycol diglycidyl ether, glycerol polyglycidyl ether, propylene glycol diglycidyl ether and polypropylene glycol diglycidyl ether can be used.

By using these specific internal cross-linking agents in combination, it is possible to further optimize the internal cross-linking structure of the super absorbent polymer to further improve liquid permeability and rewetting property, while maintaining excellent absorption characteristics.

These first and second internal cross-linking agents may be included at a concentration of 0.01 to 0.5 wt % based on the monomer composition, in combination, so that the polymerized polymer can be cross-linked.

On the other hand, in the preparation method of the embodiment, the monomer composition may further include a foaming agent, and/or a foam stabilizer.

The foaming agent causes foaming during polymerization to form pores in the hydrogel polymer, thereby increasing the surface area. As the foaming agent, a carbonate can be used. As an example, sodium bicarbonate, sodium carbonate, potassium bicarbonate, potassium carbonate, calcium bicarbonate, calcium carbonate, magnesium bicarbonate or magnesium carbonate can be used.

The foaming agent may be added at a concentration of 0.01 to 0.2 parts by weight based on 100 parts by weight of the acrylic acid-based monomer. When the amount of the foaming agent is more than 0.2 parts by weight, the number of pores may become too large, gel strength of the super absorbent polymer may decrease and density may become low, which may cause problems in distribution and storage. When the amount is less than 0.01 parts by weight, the function as the foaming agent may be insignificant.

Further, the foam stabilizer serves to uniformly distribute bubbles in the entire area of the polymer while maintaining the shape of bubbles formed by the foaming agent, which serves to increase the surface area of the polymer.

As the foam stabilizer, an anionic surfactant may be used, and examples of the anionic surfactant include sodium dodecyl sulfate, sodium stearate, ammonium lauryl sulfate, sodium lauryl ether sulfate (SLES), sodium myreth sulfate, and alkyl-ether sulfate-based compounds similar thereto. The usable anionic surfactant is not limited thereto, but preferably sodium dodecyl sulfate or sodium stearate can be used.

The anionic surfactant may be added at a concentration of 0.01 part by weight to 0.05 parts by weight based on 100 parts by weight of the acrylic acid-based monomer. When the concentration of the anionic surfactant is excessively low, the function as the foam stabilizer is insignificant and it is difficult to achieve the improvement of absorption rate. On the other hand, when the concentration is excessively high, water retention capacity and absorption rate during polymerization may be rather lowered, which is undesirable.

Meanwhile, in the preparation method of one embodiment, the monomer composition may further include an additive such as a thickener, a plasticizer, a preservation stabilizer, an antioxidant, and the like, if necessary.

The raw materials such as the acrylic acid-based monomer having at least partially neutralized acidic groups, the photopolymerization initiator, the thermal polymerization initiator, the first and the second internal cross-linking agents, and the additive may be prepared in the form of a monomer composition solution dissolved in a solvent.

At this time, any solvent which can dissolve the components may be used without limitation, and for example, one or more solvents selected from water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butyrolactone, carbitol, methylcellosolve acetate, N,N-dimethylacetamide, and the like may be used solely or in combination.

The solvent may be included in the monomer composition at a residual quantity except for the above components.

Meanwhile, the method of preparing the hydrogel polymer by thermal polymerization or photopolymerization of the monomer composition is not particularly limited if it is a common polymerization method.

Specifically, the polymerization method is largely divided into the thermal polymerization and the photopolymerization according to the energy source of the polymerization. In the case of thermal polymerization, it is generally carried out in a reactor having a kneading spindle, such as a kneader. In the case of photopolymerization, it may be carried out in a reactor equipped with a movable conveyor belt. However, the polymerization method is just an example, and the present invention is not limited thereto.

For example, as described above, the hydrogel polymer obtained by carrying out the thermal polymerization by providing hot air to a reactor equipped with a kneading spindle such as a kneader or heating the reactor is discharged from the outlet of the reactor and may have a size of centimeters or millimeters, according to the shape of the kneading spindle installed in the reactor. Specifically, the size of the obtained hydrogel polymer may vary according to the concentration and the feeding speed of the monomer composition, and generally the obtained hydrogel polymer may have a weight average diameter of about 2 to about 50 mm.

Furthermore, in the case of carrying out the photopolymerization in a reactor equipped with a movable conveyor belt, the hydrogel polymer may be obtained in the form of a sheet having a width corresponding to a width of the belt. At this time, the thickness of the polymer sheet may vary according to the concentration and the feeding speed of the monomer composition, but it is preferable to feed the monomer composition so that a polymer sheet having a thickness of about 0.5 to about 5 cm can be obtained. It is undesirable to feed the monomer composition so that the thickness of the polymer sheet becomes excessively thin, because it makes the production efficiency low, and When the thickness of the obtained polymer sheet is over 5 cm, the polymerization reaction cannot evenly occur across the thickness because of its excessively thick thickness.

Generally, the moisture content of the hydrogel polymer obtained by the above method may be about 40 to about 80 wt %. At this time, "moisture content" in the present disclosure is the content of moisture in the entire weight of the hydrogel polymer, and it means a value of which the weight of the dried polymer is subtracted from the weight of the hydrogel polymer. Specifically, the moisture content is defined as a value calculated from the weight loss due to moisture evaporation from the polymer in the process of increasing the temperature of the polymer and drying the same through infrared heating. At this time, the drying condition for measuring the moisture content is that the temperature is increased to about 180° C. and maintained at 180° C., and the total drying time is 20 min including 5 min of a heating step.

Subsequently, a step of drying the obtained hydrogel polymer is carried out.

Herein, a coarse pulverizing step may be further performed before the drying step for increasing the drying efficiency, if necessary.

The pulverizing machine used is not particularly limited. Specifically, it may be at least one selected from the group consisting of a vertical pulverizer, a turbo cutter, a turbo grinder, a rotary cutter mill, a cutter mill, a disc mill, a shred crusher, a crusher, a chopper, and a disc cutter, but it is not limited thereto.

In the pulverizing step, the hydrogel polymer may be crushed to have a diameter of about 2 to about 10 mm.

It is technically difficult to pulverize the hydrogel polymer to have a diameter of less than 2 mm because of its high moisture content, and there may be a phenomenon that the crushed particles cohere with each other. Meanwhile, when the polymer is crushed to have a diameter of larger than 10 mm, the efficiency enhancing effect in the subsequent drying step may be low.

The hydrogel polymer pulverized as above or the hydrogel polymer immediately after the polymerization without the pulverizing step is subjected to drying. At this time, the drying temperature of the drying step may be about 150 to about 250° C. When the drying temperature is lower than about 150° C., the drying time may become excessively long and the properties of the super absorbent polymer finally prepared may decrease. And when the drying temperature is higher than about 250° C., the surface of the polymer is excessively dried, and fine powders may be generated in the subsequent pulverization process and the properties of the super absorbent polymer finally prepared may decrease. Therefore, the drying process may be preferably carried out at a temperature of about 150 to about 200° C., more preferably at a temperature of about 160 to about 180° C.

Furthermore, the drying time may be about 20 to about 90 minutes in consideration of process efficiency, but it is not limited thereto.

The drying method in the drying step is not particularly limited if it has been generally used in the drying process of the hydrogel polymer. Specifically, the drying step may be carried out by the method of hot air provision, infrared radiation, microwave radiation, UV ray radiation, and the like. The moisture content of the polymer after the drying step may be about 0.1 to about 10 wt %.

Subsequently, the step of pulverizing the dried polymer obtained from the drying step is carried out.

The polymer powder obtained after the pulverization step may have a diameter of about 150 to about 850 μm. In order to pulverize the polymer into such diameter, a pin mill, a hammer mill, a screw mill, a roll mill, a disc mill, or a jog mill may be used as the pulverizer, but it is not limited thereto.

Further, in order to maintain the properties of the super absorbent polymer powder which is finally commercialized after the pulverization step, a separate process of classifying the polymer powders obtained after the pulverization according to the particle size may be carried out. The polymer powders may be classified to have a constant weight ratio according to the particle size.

After obtaining the base resin in the powder form through the above-described classification step, the base resin is heated in the presence of a surface cross-linking agent to carry out surface modification.

In the general preparation method of a super absorbent polymer, a surface cross-linking solution containing a surface cross-linking agent is mixed with a dried, pulverized and classified polymer, that is, a base resin, and then the mixture is heated to carry out a surface cross-linking reaction of the pulverized polymer.

The surface cross-linking step is a step of inducing a cross-linking reaction on the surface of the pulverized polymer in the presence of a surface cross-linking agent to form a super absorbent polymer having improved physical properties. Through the surface cross-linking, a surface cross-linked layer (surface modified layer) is formed on the surface of the pulverized and classified polymer particles.

Generally, surface cross-linking agents are applied on the surface of the base resin particles, so that surface cross-linking reactions occur on the surface of the base resin particles, which improves cross-linkability on the surface of the particles without substantially affecting the interior of the particles. Therefore, the surface cross-linked super absorbent polymer particles have a higher degree of cross-linking near the surface than in the interior, as the cross-linked polymer on the surface of the base resin is further cross-linked.

Meanwhile, the surface cross-linking agent is a compound capable of reacting with functional groups of the base resin. For example, polyalcohol-based compounds, polyepoxy-based compounds, polyamine compounds, haloepoxy compounds, condensates of haloepoxy compounds, oxazoline-based compounds, or alkylene carbonate compounds may be used without particular limitations.

Specific examples of the polyalcohol-based compound may include one or more selected from the group consisting of di-, tri-, tetra- or polyethylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexane dimethanol.

Further, the polyepoxy-based compound may include ethylene glycol diglycidyl ether, glycidol and the like. The polyamine compound may include one or more selected from the group consisting of ethylene diamine, diethylene triamine, triethylene tetraamine, tetraethylene pentamine, pentaethylene hexamine, polyethylene imine, and polyamide polyamine.

Further, the haloepoxy compound may include epichlorohydrin, epibromohydrin, or α-methylephichlorohydrin. Meanwhile, the mono-, di-, or polyoxazolidinone compound may include, for example, 2-oxazolidinone and the like.

Further, the alkylene carbonate-based compound may include ethylene carbonate, and the like. These may be used alone or in combination with each other.

The amount of the surface cross-linking agent added may be appropriately selected depending on the kind of the surface cross-linking agent added or the reaction conditions. However, the surface cross-linking agent may be generally used in an amount of about 0.001 to about 5 parts by weight, preferably about 0.01 to about 3 parts by weight, and more preferably about 0.05 to about 2 parts by weight, based on 100 parts by weight of the base resin.

When the amount of the surface cross-linking agent is excessively small, the surface cross-linking reaction hardly occurs, and when the amount is higher than 5 parts by weight based on 100 parts by weight of the polymer, the absorbency such as water retention capacity may be deteriorated due to excessive surface cross-linking reaction.

When the surface cross-linking agent is added, water may be further mixed together and added in the form of a surface cross-linking solution. When water is added, there is an advantage that the surface cross-linking agent can be uniformly dispersed in the polymer. Herein, the added amount of water is preferably 1 to 10 parts by weight based on 100 parts by weight of the polymer in order to optimize a surface penetration depth of the surface cross-linking agent, while inducing even dispersion of the surface cross-linking agent and preventing the polymer powder from aggregating.

Meanwhile, the surface cross-linking step (surface modification step) described above may be carried out by using a polyvalent metal salt, for example, an aluminum salt, more specifically at least one selected from the group consisting of a sulphate, potassium salt, ammonium salt, sodium salt, and hydrochloride of aluminum, in addition to the above-mentioned surface cross-linking agent.

As the polyvalent metal salt is further used, it is possible to optimize gel strength of the super absorbent polymer prepared by the method of one embodiment, or the cross-linking structure of the surface cross-linked layer. As a result, absorption ability under pressure or liquid permeability and the rewetting property of the super absorbent polymer can be further improved. The polyvalent metal salt may be added to the surface cross-linking solution together with the surface cross-linking agent, and may be used in an amount of 0.01 to 4 parts by weight, 0.05 to 1 part by weight, 0.1 to 0.5 parts by weight, or 0.15 to 0.3 parts by weight, based on 100 parts by weight of the base resin.

Meanwhile, the surface modification step is performed on the base resin by heating the mixture of the base resin and the surface cross-linking solution.

The surface modification step may be carried out under well-known conditions depending on the kind of the surface cross-linking agent, for example, at a temperature of 100 to 200° C. for 20 to 60 minutes. In a more specific example, when the surface cross-linking agent is a polyvalent epoxy compound, it may be carried out by heating at 120 to 180° C., or 120 to 150° C. for 10 to 50 minutes, or 20 to 40 minutes. When the temperature of the surface modification step is less than 100° C. or the reaction time is too short, the surface cross-linking reaction may not occur properly and transmittancy may be lowered. When the temperature exceeds 200° C. or the reaction time is too long, water retention ability may be lowered.

The heating means for the surface cross-linking reaction is not particularly limited. It is possible to provide a thermal media thereto or provide a heat source directly thereto. At this time, usable thermal media may be a heated fluid such as steam, hot air, hot oil, and the like, but the present invention is not limited thereto. Furthermore, the temperature of the thermal media provided thereto may be properly selected in consideration of the means of the thermal media, heating speed, and target temperature of heating. Meanwhile, an electric heater or a gas heater may be used as the heat source provided directly, but the present invention is not limited thereto.

When the above-mentioned surface modification step is carried out, a super absorbent polymer can be finally produced according to the method of one embodiment. This super absorbent polymer can exhibit improved rewetting property, excellent water retention ability, absorption ability under pressure and absorption rate, and the like, as it has an optimized internal cross-linking structure by using the specific internal cross-linking agents in combination.

The super absorbent polymer prepared by the above method includes:
a base resin including a cross-linked polymer obtained by cross-linking an acrylic acid-based monomer having at least partially neutralized acidic groups by a medium of an internal cross-linking agent;
a surface cross-linked layer formed on a particle surface of the base resin, wherein the cross-linked polymer is additionally cross-linked by a medium of a surface cross-linking agent; and
a polyvalent metal salt formed on the surface cross-linked layer,
wherein the internal cross-linking agent comprises a poly(meth)acrylate of polyols-based first internal cross-linking agent and a polyglycidyl ether of polyols-based second internal cross-linking agent in a weight ratio of 1:20 to 1:300.

As described above, the polyvalent metal salt such as an aluminum salt is optionally used in the surface cross-linking, so that the super absorbent polymer further includes a polyvalent metal salt formed on the surface cross-linked layer. This polyvalent metal salt such as an aluminum salt is already described above, and further explanation is omitted.

The super absorbent polymer can basically exhibit absorption properties such as excellent water retention capacity, absorption ability under pressure and absorption rate.

For example, the super absorbent polymer may have water retention capacity (CRC) of 26 g/g or more, 27 g/g or more, or 30 g/g or more, and 40 g/g or less, 38 g/g or less, or 35 g/g or less, as measured according to EDANA method WSP 241.3.

In addition, the super absorbent polymer prepared according to the method above may have absorption ability under pressure (AUP) at 0.7 psi of 8 g/g or more, 10 g/g or more, or 11 g/g or more, and 30 g/g or less, 20 g/g or less, or 17 g/g or less, as measured according to EDANA method WSP 242.3.

In addition, the super absorbent polymer prepared according to the method above may have a water-soluble component content of 10 wt % or less, 8 wt % or less, or 7 or less, and 0 wt % or more, 1 wt % or more, or 3 wt % or more, as measured according to EDANA method WSP 270.2.

The super absorbent polymer prepared according to the method above may have a vortex time of 40 seconds or less, 38 seconds or less, or 35 seconds or less. Since the lower vortex time can be evaluated as the better, the lower limit is theoretically 0 seconds, but may be 5 seconds or more, 10 seconds or more, or 15 seconds or more.

The vortex time refers to the time required (unit:second) for the vortex of the liquid to disappear due to the rapid absorption when the super absorbent polymer is added to physiological saline and stirred. It can be seen that the shorter the time, the faster the initial absorption rate of the super absorbent polymer.

Meanwhile, the super absorbent polymer can exhibit improved rewetting property while having excellent absorption properties. More specifically, the super absorbent polymer may have a rewetting property of 1.0 g or less, 0.9 g or less, or 0.8 g or less, and 0.1 g or more, 0.15 g or more, or 0.25 g or more. The rewetting property refers to the weight of water came out from the super absorbent polymer to the filter paper, after immersing 1 g of the super absorbent polymer in 100 g of tap water, swelling for 10 minutes, and leaving it on a filter paper for 50 minutes. The electrical conductivity of the tap water used in the measurement of the rewetting property may be in the range of 170 to 180 µS/cm, and the electrical conductivity may be measured using, for example, an electrical conductivity meter such as Orion Star A222 (manufactured by Thermo Scientific). For reference, the electrical conductivity of the tap water has a great influence on the physical properties of the product, so the tap water having equivalent electrical conductivity should be used for the rewet measurement.

The above-mentioned super absorbent polymer has excellent absorption characteristics, and the rewetting and urine leakage phenomenon can be reduced even when a large amount of urine is absorbed.

Hereinafter, the present invention will be described in more detail with reference to examples. However, these examples are for illustrative purposes only, and the invention is not intended to be limited by these examples.

EXAMPLES

Preparation of Super Absorbent Polymer

Comparative Example 1

After putting 470.5 g of acrylic acid, 9000 ppm of an internal cross-linking agent (PEGDA 400, polyethylene glycol diacrylate 400) and 80 ppm of a photoinitiator (diphenyl (2,4,6-trimethylbenzoyl)-phosphine oxide) in a 3 L glass container equipped with a stirrer and a thermometer and dissolving the same, an aqueous solution of the water-soluble unsaturated monomer (degree of neutralization: 70 mol %; solid content: 45 wt %) was prepared by adding 805.6 g of a 24.5% sodium hydroxide solution. When the temperature of the aqueous solution of the water-soluble unsaturated monomer became 45° C. due to the heat of neutralization, 250 ppm of a surfactant, sodium dodecyl sulfate, was added. Thereafter, when the temperature of the aqueous solution reached 43° C., it was immersed in a container containing 0.15% of SBC and 0.12% of SPS, followed by irradiating with ultraviolet rays for 1 minute (irradiation amount: 10 mV/cm$^2$) to perform UV polymerization to obtain a hydrogel polymer. The obtained hydrogel polymer was pulverized into a size of 2 mm*2 mm, and the moisture content thereof was 40.1%.

The obtained gel-type resin was spread on a stainless wire gauze having a hole size of 600 µm to a thickness of about 30 mm, and dried in a 180° C. hot air oven for 30 minutes. The dried polymer was pulverized using a pulverizer and classified with a standard mesh of ASTM standard to obtain a base resin having a particle size of 150 to 850 µm.

A surface cross-linking solution containing 0.02 parts by weight of polyethylene glycol diglycidyl ester (EJ1030S) as a surface cross-linking agent, 8 parts by weight of water, 5 parts by weight of methanol, 0.05 parts by weight of sodium metabisulfite ($Na_2S_2O_5$) as a reductant and 0.2 parts by weight of aluminum sulfate was sprayed onto 100 parts by weight of the base resin and mixed. The mixture was put into a container equipped with a stirrer and a double jacket, and a surface cross-linking reaction was carried out at 140° C. for 30 minutes. Then, the surface-treated powder was classified with a standard mesh of ASTM standard to obtain a super absorbent polymer powder having a particle size of 150 to 850 μm.

Example 1

A super absorbent polymer powder was obtained in the same manner as in Comparative Example 1, except that 60 ppm of PEGDA 400 (polyethylene glycol diacrylate 400) and 2500 ppm of ethylene glycol diglycidyl ether (EJ1030) (first internal cross-linking agent:second internal cross-linking agent=1:41.7) were used together as an internal cross-linking agent in the aqueous solution of the water-soluble unsaturated monomer.

Example 2

A super absorbent polymer powder was obtained in the same manner as in Comparative Example 1, except that 30 ppm of PEGDA 400 (polyethylene glycol diacrylate 400) and 2700 ppm of ethylene glycol diglycidyl ether (EJ1030) (first internal cross-linking agent:second internal cross-linking agent=1:90) were used together as an internal cross-linking agent in the aqueous solution of the water-soluble unsaturated monomer.

Example 3

A super absorbent polymer powder was obtained in the same manner as in Comparative Example 1, except that 100 ppm of PEGDA 400 (polyethylene glycol diacrylate 400) and 2700 ppm of ethylene glycol diglycidyl ether (EJ1030) (first internal cross-linking agent:second internal cross-linking agent=1:27) were used together as an internal cross-linking agent in the aqueous solution of the water-soluble unsaturated monomer.

Example 4

A super absorbent polymer powder was obtained in the same manner as in Comparative Example 1, except that 10 ppm of PEGDA 400 (polyethylene glycol diacrylate 400) and 2400 ppm of ethylene glycol diglycidyl ether (EJ1030) (first internal cross-linking agent:second internal cross-linking agent=1:240) were used together as an internal cross-linking agent in the aqueous solution of the water-soluble unsaturated monomer.

Comparative Example 2

A super absorbent polymer powder was obtained in the same manner as in Comparative Example 1, except that 4000 ppm of PEGDA 400 (polyethylene glycol diacrylate 400) and 1500 ppm of ethylene glycol diglycidyl ether (EJ1030) (first internal cross-linking agent:second internal cross-linking agent=2.7:1) were used together as an internal cross-linking agent in the aqueous solution of the water-soluble unsaturated monomer.

Comparative Example 3

A super absorbent polymer powder was obtained in the same manner as in Example 1, except that aluminum sulfate was not used in the preparation of the surface cross-linking solution.

Experimental Examples

The physical properties of the super absorbent polymers prepared in the above Examples and Comparative Examples were evaluated by the following methods.

Unless otherwise indicated, all of the following physical properties were evaluated at room temperature (25° C.), and physiological saline or salt water refers to a 0.9 wt % sodium chloride (NaCl) aqueous solution.

(1) Centrifuge Retention Capacity (CRC)

The CRC of each resin was measured in accordance with EDANA WSP 241.3.

Specifically, $W_0(g)$ (about 0.2 g) of the super absorbent polymer was uniformly placed into a non-woven bag, sealed, and then immersed in physiological saline (0.9 wt %) at room temperature. After 30 minutes, residual water was drained from the bag by centrifugal device under the condition of 250 G for 3 minutes, and the weight $W_2(g)$ of the bag was measured. In addition, the same manipulation was performed without the polymer, and the weight $W_1(g)$ of the bag was measured. The CRC (g/g) was calculated by using the obtained weight values according to the following Equation.

$$CRC(g/g) = \{[W_2(g) - W_1(g)]/W_0(g)\} - 1 \quad \text{[Equation 1]}$$

(2) Absorbency Under Pressure (AUP)

The AUP at 0.3 psi of each resin was measured in accordance with EDANA WSP 242.3.

Specifically, a 400 mesh stainless steel net was installed in a cylindrical bottom of a plastic having an internal diameter of 25 mm. $W_0(g, 0.90 g)$ of the absorbent polymer was uniformly scattered on the steel net under the conditions of room temperature and humidity of 50%, and a piston which can provide a load of 0.7 psi uniformly was put thereon. The external diameter of the piston was slightly smaller than 25 mm, there was no gap between the cylindrical internal wall and the piston, and the jig-jog of the cylinder was not interrupted. At this time, the weight $W_3(g)$ of the device was measured.

After putting a glass filter having a diameter of 90 mm and a thickness of 5 mm in a Petri dish having a diameter of 150 mm, physiological saline composed of 0.90 wt % sodium chloride was poured in the dish until the surface level became equal to the upper surface of the glass filter. A filter paper having a diameter of 90 mm was put thereon. The measuring device was put on the filter paper and the solution was absorbed under a load for about 1 hour. After 1 hour, the weight $W_4(g)$ was measured after lifting the measuring device up.

The AUP (g/g) was calculated by using the obtained weight values according to the following Equation 2.

$$AUP(g/g) = [W_4(g) - W_3(g)]/W_0(g) \quad \text{[Equation 2]}$$

(3) Absorption rate (Vortex)

The absorption rate (vortex) was measured in seconds in accordance with the method described in International Patent Application Publication No. 1987-003208.

Specifically, 2 g of the super absorbent polymer was put in 50 mL of physiological saline at 23 to 24° C., and then stirred with a magnetic bar (diameter 8 mm, length 30 mm) at 600 rpm. The time required for the vortex to disappear was measured in seconds.

(4) Water-Soluble Component Content

The water-soluble component content was measured in accordance with EDANA method WSP 270.2.

(5) No-Pressure Tap Water Short-Term Rewetting Property (1 hr)

The short-term rewetting property was measured by the following method. In the measurement of the rewetting property, tap water having an electrical conductivity of 170 to 180 μS/cm was used. The electrical conductivity was measured using an electrical conductivity meter of Orion Star A222 (manufactured by Thermo Scientific).

① 1 g of a super absorbent polymer was placed in a cup (upper diameter 7 cm, lower diameter 5 cm, height 8 cm, volume 192 ml), and 100 g of tap water was poured thereto and swelled.

② Ten minutes after the tap water was poured, the cup containing the swollen super absorbent polymer was turned upside down on top of 5 filter papers (manufactured by Whatman, catalog No. 1004-110, pore size 20-25 μm, diameter 11 cm).

③ 60 minutes after the tap water was poured, the cup and the super absorbent polymer were removed, and the amount of tap water (unit: g) of the filter paper was measured.

The physical properties of the Examples and Comparative Examples are shown in Table 1 below.

TABLE 1

| | CRC (g/g) | AUP at 0.7 psi (g/g) | Vortex (sec) | Water-soluble component content (wt %) | No-pressure tap water short-term rewetting property (g) |
|---|---|---|---|---|---|
| Example 1 | 30.3 | 11.3 | 28 | 4.8 | 0.42 |
| Example 2 | 33.4 | 8.9 | 35 | 6.6 | 0.3 |
| Example 3 | 27.3 | 12.5 | 28 | 4.9 | 0.7 |
| Example 4 | 31.3 | 10.9 | 29 | 5.0 | 0.39 |
| Comparative Example 1 | 30.2 | 11.5 | 21 | 6.5 | 1.4 |
| Comparative Example 2 | 29.1 | 11.0 | 25 | 9.1 | 1.3 |
| Comparative Example 3 | 30.3 | 9.3 | 32 | 5.0 | 0.8 |

Referring to Table 1, Examples 1 to 3 exhibited the same water retention capacity, absorption capacity under pressure and absorption rate as those of Comparative Examples 1 and 2. It was also confirmed that they had much smaller amount of rewetting with respect to tap water than that of Comparative Examples, indicating improved rewetting property.

In addition, Comparative Example 3 is about the super absorbent polymer prepared without using the polyvalent metal salt (aluminum sulfate) of the Example 1, and was confirmed to be poor in absorption ability under pressure and rewetting property as compared with Examples.

The invention claimed is:

1. A super absorbent polymer, comprising:
   a base resin comprising a cross-linked polymer obtained by cross-linking an acrylic acid-based monomer having at least partially neutralized acidic groups by a medium of an internal cross-linking agent;
   a surface cross-linked layer formed on a particle surface of the base resin, wherein the cross-linked polymer is additionally cross-linked by a medium of a surface cross-linking agent; and
   a polyvalent metal salt formed on the surface cross-linked layer,
   wherein the internal cross-linking agent comprises a poly(meth)acrylate of polyols-based first internal cross-linking agent and a polyglycidyl ether of polyols-based second internal cross-linking agent in a weight ratio of 1:20 to 1:300.

2. The super absorbent polymer of claim 1, wherein the polyvalent metal salt comprises an aluminum salt.

3. The super absorbent polymer of claim 1, wherein a rewetting property of the super absorbent polymer, is 1.0 g, wherein the rewetting property is a weight of water came out from the super absorbent polymer after immersing 1 g of the super absorbent polymer in 100 g of tap water, swelling for 10 minutes, and leaving it on a filter paper for 50 minutes.

4. The super absorbent polymer of claim 1, wherein the acrylic acid-based monomer comprises acrylic acid, methacrylic acid, or a monovalent metal salt, a divalent metal salt, an ammonium salt, or an organic amine salt thereof.

* * * * *